US005533402A

United States Patent [19]

Sarvazyan et al.

[11] Patent Number: 5,533,402
[45] Date of Patent: Jul. 9, 1996

[54] METHOD AND APPARATUS FOR MEASURING ACOUSTIC PARAMETERS IN LIQUIDS USING CYLINDRICAL ULTRASONIC STANDING WAVES

[75] Inventors: Armen Sarvazyan, East Brunswick, N.J.; Viktor Ponomarev, Rostov-on-Don, Russian Federation

[73] Assignee: Artann Corporation, Harvard, Me.

[21] Appl. No.: 240,831

[22] Filed: May 11, 1994

[51] Int. Cl.[6] .................................................. G01H 5/00
[52] U.S. Cl. .................................................. 73/645; 73/579
[58] Field of Search .......................... 73/579, 571, 645, 73/647, 19.03, 24.01, 24.06, 31.05, 61.45, 61.49, 64.53

[56] References Cited

U.S. PATENT DOCUMENTS

| 3,925,692 | 12/1975 | Lechek et al. | 310/8.7 |
| 4,009,616 | 3/1977 | Wonn | 73/398 |
| 4,107,479 | 8/1978 | Heil | 179/116 |
| 4,145,450 | 3/1979 | Winder et al. | 426/231 |
| 4,242,912 | 1/1981 | Burckhardt et al. | 73/626 |
| 5,081,391 | 1/1992 | Owen | 73/632 |
| 5,099,454 | 3/1992 | Dieulesaint et al. | 367/99 |

OTHER PUBLICATIONS

J. R. Barker et al., "The Velocity and Attenuation of Sound in Solid Argon," 3 *Can. J. Phys.* 397 (1955).

E. R. Dobbs et al., "Measurement of the Velocity of Sound in Liquid Argon and Liquid Nitrogen at High Pressures," 32 *Journal of the Acoustical Society of America* 1215 (1960).

A. P. Sarvazyan, "Development of Methods of Precise Ultrasonic Measurement in Small Volumes of Liquids," 20 *Ultrasonics* 151 (1982).

F. Eggers et al., "New Acoustic Resonator for Liquids in the 0.2— to 2–MHz Range," 57 *J. Acoust. Soc. Am.* 331 (1975).

F. Eggers et al., "High Q Ultrasonic Liquid Resonators with Concave Transducers," 47 *Rev. Sci. Instrum.* 361 (1976).

F. Eggers, "Ultrasonic Velocity and Attenuation Measurements in Liquids With Resonators, Extending the MHz Frequency Range," 76 *Acustica* 231 (1992).

Publication No. ESD–619, Model 6080 Nusonics Concentration Analyzer, Mapco, Inc. (Jul. 15, 1980).

N. Inoue wt al., "Ultrasonic Velocity Measurement of Liquids in the Frequency Range 0.2 . . . 7 MHz Using an Improved Ultrasonic Interferometer," 74 *Acustica* 128 (1991).

A. P. Sarazyan et al., "Theoretical Analysis of an Ultrasonic Interferometer for Precise Measurements at High Pressures," 29 *Ultrasonics* 119 (1991).

Operating Manual of Model PLR–1000 Pulsed Phase Locked Loop Ultrasonic Interferometer, MicroUltrasonics, Inc. (No Date).

Lynnworth, "Industrial Applications of Ultrasound—A Review II. Measurements, Tests, and Process Control Using Low–Intensity Ultrasound," *IEEE Trans. on Sonics and Ultrasonics* 71 (Mar. 1975).

(List continued on next page.)

*Primary Examiner*—Richard Chilcot
*Assistant Examiner*—Max H. Noori
*Attorney, Agent, or Firm*—Wigman, Cohen, Leitner & Myers

[57] ABSTRACT

Methods and apparatus are disclosed for analyzing liquids utilizing cylindrical acoustic standing waves, generally in the ultrasonic region. The invention facilitates measurement of acoustic parameters of a fluid, such as sound velocity and attenuation, which themselves serve as indicators of solute concentrations and various ongoing chemical processes occurring. In preferred embodiments of the invention, cylindrical ultrasonic standing waves are generated in a liquid contained within a cylindrical housing by causing coherent oscillation of the entire cylinder, or a circumferential segment thereof, or multiple circumferential segments thereof. The invention is amenable to a variety of applications and implementations, most involving pairs of resonators, one containing a sample of the liquid under study, and the other containing a reference liquid.

18 Claims, 10 Drawing Sheets

OTHER PUBLICATIONS

F. Eggers et al., "Ultrasonic Measurements with Milliliter Liquid Samples in the 0.5–100 MHz Range," 44 *Rev. Sci. Instrum.* 969 (1973).

Paper from Staveley Sensors Inc., on EBL Piezoceramic Tube Actuators (Undated).

A. P. Sarvazyan, "Ultrasonic Velocimetry of Biological Compounds," 20 *Annu. Rev. Biophys. Chem.* 321 (1991).

F. Eggers et al., "Ultrasonic Methods," 16 *Methods in Enzymology* 55 (1969).

A. J. Matheson, "Experimental Methods of Studying Ultrasonic Propagation," 3 *Molecular Acoustics* 18 (1970).

E. P. Papadakis, "Ultrasonic Velocity and Attenuation: Measurement Methods with Scientific and Industrial Applications," 12 *Physical Acoustics* 277 (1976).

Austrian illustration of SPR 4114 and SPR 4122 Konzentrations-MeBzellen (undated).

METHOD AND APPARATUS FOR MEASURING ACOUSTIC PARAMETERS IN LIQUIDS USING CYLINDRICAL ULTRASONIC STANDING WAVES

BACKGROUND OF THE INVENTION

1. Field of the Invention

The present invention relates to acoustic analysis of liquids, and more particularly to the use of resonant ultrasonic fields to determine the concentration of a dissolved species.

2. Description of the Related Art

Just as electromagnetic energy has been widely exploited in the measurement of physicochemical properties of gases, liquids and solids, so too have sound waves. Ultrasound, in the upper kilohertz and megahertz frequency bands, has proven especially useful for studying liquids. The acoustic properties of a liquid — in particular, the velocity and attenuation of an ultrasonic pressure wave through the liquid — depend on, and therefore can be used to measure, various thermodynamic and kinetic characteristics. Sound velocity, for example, provide information about adiabatic compressibility and density. Attenuation of sound in the medium provides information about the kinetic and thermodynamic parameters of relaxation processes. Both the velocity and attenuation of ultrasound are frequently observed to monitor chemical processes occurring in solution and to determine solute concentrations.

A wide variety of ultrasonic instrumentation has been developed for specialized research purposes. Essentially, these instruments include means for generating a sound wave in the material to be studied, and means for measuring reporting changes in the sound wave as it propagates through and interacts with the material. Devices intended to analyze liquids generally make use of a pair of piezoelectric transducers, one of which generates the acoustic signal and the other of which detects the signal after it has traveled through the liquid under study. The acoustic signal may take many forms, e.g., a pulse wave, a continuous traveling wave or a continuous standing wave; the frequency of the applied field may be varied or kept constant; and the measured parameters may include amplitude, phase and/or frequency.

Plane-wave resonators are a common type of instrument for ultrasonic analysis of liquids. These devices may comprise a chamber having plane piezotransducers along two opposed, precisely parallel walls. A plane pressure wave is generated by one transducer and progresses through the liquid to the other transducer, where it is detected and reflected back to the first transducer. At certain fundamental frequencies determined primarily by the distance between transducers and the acoustic properties of the contained liquid, the traveling transmitted and reflected waves combine into the stationary pattern characteristic of a standing wave. The standing wave condition results in delivery by the detection transducer of large voltage peaks.

In operation, once the standing wave is achieved, one changes the applied frequency and plots (or otherwise monitors) the amplitude and phase at the detecting transducer as a function of applied frequency. This information facilitates calculation of the primary acoustic parameters of the liquid, namely, the velocity and attenuation of sound. These parameters, in turn, can provide information on characteristics such as concentration. The plane-wave resonator has also been used to measure the thermodynamic properties of a liquid (since the velocity of sound is a simple function of the second derivative of free energy with respect to pressure, and therefore the profile of sound velocity at different temperatures and pressures can be used to derive the equation of state).

Acoustic absorption occurs as a result of irreversible interaction of ultrasonic pressure waves with a liquid and/or with a chemical species in the liquid. To distinguish between the absorption due to the pure liquid and to a dissolved species, one compares the absorption characteristics of the solution against that of the pure solvent, both measured at the same temperature and in the same resonator cell. The degree to which absorption of the solution exceeds that of the pure solvent reflects the contribution of the solute, and therefore its concentration.

To measure absorption using the plane-wave resonator, one typically activates the driven transducer and adjusts the frequency until a standing wave is observed. The amplitude and resonance frequency fn are measured at peak output voltage (resonance) and at oscillation frequencies above and below resonance where the amplitude falls 3 db below peak (the half-power level). This procedure is executed for the pure solvent and, separately, for the sample under study.

An important characteristic of a resonator is its quality factor, Q, defined as the ratio of the resonance frequency to the half-power frequency band, $f_n/\Delta f_n$. Q is inversely proportional to the total energy loss in the resonator system, which includes, in addition to attenuation due to the liquid, losses from beam divergence, scattering, friction, imperfect reflection, and transducer mounting and coupling. High Q-factors are associated with symmetry and smoothness of sharp resonance peaks and definite separations of resonance peaks in the frequency scale.

Solute concentration may be derived from comparison of the measured Q-factors of the pure solvent and that of the solution. Investigations of fast chemical reactions and relaxation processes occurring in solution, by contrast, generally involve measurement of the absorption over a range of frequencies.

Measurements of acoustic velocity in a liquid are made primarily to evaluate elastic properties, such as compressibility. The natural resonance frequencies of a liquid-containing resonator are linearly related to the ultrasound velocity. These frequencies may be determined by identifying output-voltage maxima (as described above) or by determining the inflection points of a phase-frequency plot. For solutions, the relative difference between sound velocities in a reference liquid (e.g., a pure solvent) and a sample liquid (e.g., a solution) is a linear function of the relative difference between resonance frequencies of the liquids according to the relation $$(V_s-V_r)/V_r=(f_{ns}-f_{nr})/f_{nr}$$

where $V_r$ is the velocity of sound in the reference liquid, $V_s$ is the velocity in the sample liquid, and $f_{nr}$ and $f_{ns}$ are resonance frequencies of the reference and sample liquids, respectively. The sound velocity of a sample is calculated using resonance-frequency measurements and knowledge of the sound velocity in the reference liquid.

Plane-wave resonators, while common, suffer from a number of disadvantages, one of which is the necessity for complex constructions to achieve and maintain the parallelism conditions required to support standing waves. Plots of amplitude as a function of frequency obtained with improperly adjusted plane-wave resonators often exhibit field distortions, which may be manifested as "humps" indicative of the presence of unwanted interference effects, spurious modes, reflective side walls, or misalignment of the plane transducers. This is due in large part to the mechanical difficulty of achieving and maintaining precise alignment among the various resonator components. Also, the production of adequate standing-wave patterns requires transducer diameters that are much larger than the wavelength (typically, the ratio of diameter to wavelength exceeds 20), thus placing relatively large lower limits on resonator volumes.

Resonators of all types are vulnerable to temperature drift, since the fluid wavelength of sound in the fluid is highly temperature-dependent. Thermostating capability, therefore, is frequently crucial. For example, in water, a change of 1° C. alters the speed of sound by approximately 0.15%, altering the resonance wavelength by the same proportion; this shift is significantly greater than the resonance range, and will therefore drive the system out of resonance. For example, using a water-filled resonator operating at a resonance frequency of 10 MHz, the half-power bandwidth (i.e., the effective resonance range) is approximately 1 kHz; a change in temperature of as little as 0.066° C. is sufficient to drive the system outside this bandwidth. See Eggers et al., "Ultrasonic Measurements with Milliliter Liquid Samples in the 0.5–100 MHz Range," 44 Rev. Sci. Instr. 969 (1973).

DESCRIPTION OF THE INVENTION

Objects of the Invention

It is, therefore, an object of the invention to facilitate measurement of the acoustic parameters of a liquid using apparatus that is simple in design and which minimizes field distortions.

It is another object of the invention to facilitate measurement of the acoustic parameters of a liquid using apparatus that does not require mechanical adjustment of the resonator.

It is still another object of the invention to facilitate measurement of the acoustic parameters of a liquid in small volumes unachievable with existing equipment.

It is yet a further object of the invention to provide an ultrasonic measurement apparatus that delivers stable standing waves without the need for high-precision thermostating capability.

Other objects will, in part, be obvious and will, in part, appear hereinafter. The invention accordingly comprises an article of manufacture possessing the features and properties exemplified in the constructions described herein and the several steps and the relation of one or more of such steps with respect to the others and the apparatus embodying the features of construction, combination of elements and the arrangement of parts that are adapted to effect such steps, all as exemplified in the following summary and detailed description, and the scope of the invention will be indicated in the claims.

BRIEF SUMMARY OF THE INVENTION

The invention utilizes cylindrical acoustic standing waves, generally in the ultrasonic region of frequencies, to measure acoustic parameters of a fluid (a liquid, most commonly, or a gas) such as sound velocity and attenuation. These parameters facilitate determination of solute concentrations and allow various physical and chemical processes occurring in a fluid to be monitored.

In preferred embodiments of the invention, cylindrical ultrasonic standing waves are generated in a fluid contained within a cylindrical housing by causing coherent oscillation of the entire cylinder, or a circumferential segment thereof, or multiple circumferential segments thereof.

A central component of the present invention is the cylindrical resonator used to contain fluid and generate cylindrical standing waves therein. The resonator may be a radially polarized, cylindrical piezoelectric tube having a set of associated electrodes, or a nonpiezoelectric (e.g., glass, plastic or steel) tube acoustically coupled to a source of oscillation. Either type of resonator is easily manufactured, and provides the symmetry necessary for generation of cylindrical standing waves without the need for delicate adjustment assemblies. That symmetry also largely avoids the field distortions that occur at the edges of planar resonators. The electrodes associated with our resonator are connected to electrical circuitry to both cause and detect oscillation, and to report acoustic parameters. The invention also features a feedback system that ensures maintenance of the standing wave condition notwithstanding temperature and other environmental variations that cause drift of the resonance frequency.

The apparatus of the invention can be constructed to admit and operate on very small volumes, thereby facilitating a wide range of biological manipulations and assays for which only very small samples are available. For example, volumes of 10 µl or less are readily achieved. The invention is also amenable to a variety of applications and implementations. Most of these involve pairs of resonators, one containing a sample of the liquid under study, and the other containing a reference liquid.

In one implementation, a "dip-in" probe includes a sealed resonator chamber containing the reference liquid and a carrier for a second, identical resonator that may be immersed directly in a reservoir of the sample liquid. In a related "fill-in" implementation, configured as a syringe, facilitates suction withdrawal of liquid from a reservoir into the resonator. Other implementations facilitate acoustic analysis of liquids at elevated surrounding pressures, at different temperatures and on a continuous-flow basis. The invention also facilitates simultaneous analysis of particle suspensions and the particle-free liquid carrier.

The invention is also amenable to a variety of control and reporting configurations. These may be as simple as meters that indicate amplitude and/or frequency, but may also extend to computer-executed algorithms for calculating user-specified acoustic parameters from measured quantities. The invention can also include programmable software that, in response to user selection of a desired parameter, directs the execution of the various appropriate measurements as well as processing of the data obtained therefrom to report a final value.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

1. Basic Apparatus and Operation

Figure 1:
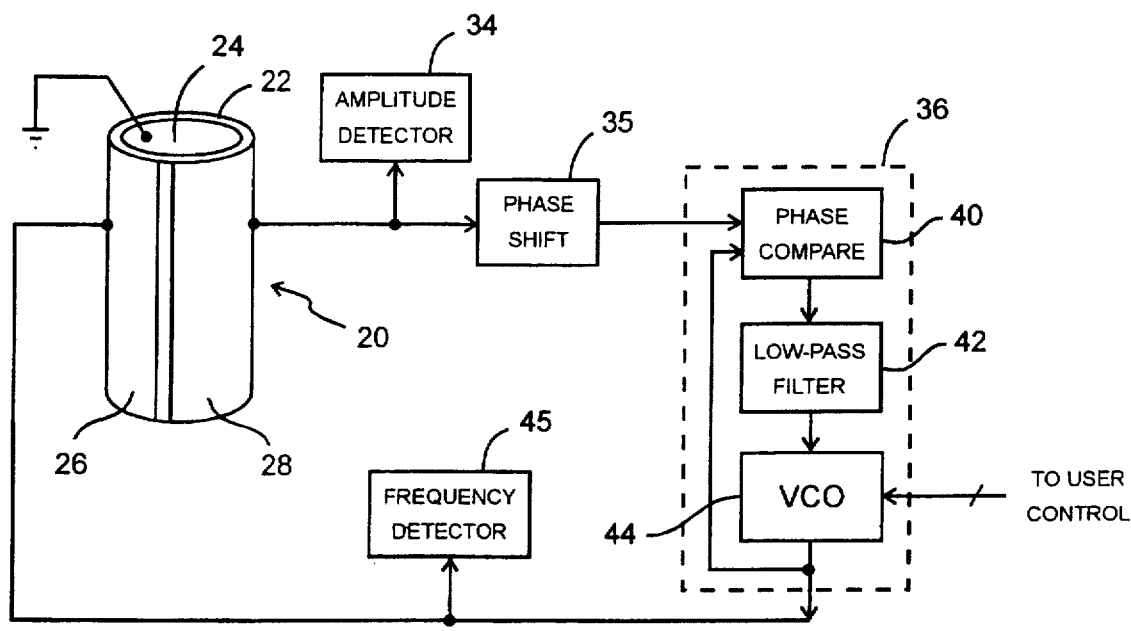
FIG. 1 is a partially schematic representation of a first embodiment of the inventive resonator, which features a three-electrode transducer (shown in isometric view)

Refer first to FIG. 1, which illustrates the components of the first resonator embodiment of the present invention connected to simple oscillation and feedback circuitry. The depicted circuit contains a tubular transducer, denoted generally by reference numeral 20, that includes a cylinder 22 of piezoelectric material (e.g., radially polarized barium titanate ceramic, suitable preformed cylinders of which are available, for example, from Staveley Sensors Inc., Hartford, Conn.), or a non-piezoelectric (e.g., glass or plastic) tube in contact with or at least partially surrounded by a piezoelectric film layer, plated with metal (such as nickel) to form surface electrodes. Specifically, the entire interior surface of sensor 20 is plated to form an inner electrode 24, which is grounded; and the outer surface of transducer 20 includes at least two circumferential electrodes 26, 28. These outer electrodes are spaced apart from one another on the surface of cylinder 22. The transducer may be provided with electrodes simply by plating the interior and exterior surfaces of cylinder 22, then removing narrow exterior lanes of plating to create the depicted pattern.

The illustrated circuit also includes a phase shifter 35 and a phase-locked loop 36, which consists of a phase comparator 40, a low-pass filter 42, and a voltage-controlled oscillator (VCO) 44. Electrode 28, which serves as the detection electrode, is connected to an amplitude-measurement device or detector 34, such as a meter, an oscilloscope or a computer (through suitable analog-to-digital conversion circuitry) and to a first input terminal of comparator 40 via phase shifter 35. Measurement device 34 includes appropriate low-pass or smoothing filter circuitry to ensure a reliable signal. An output terminal of comparator 40 is connected to the input terminal of low-pass filter 42, and the output terminal of the latter component is connected VCO 44. The output terminal of VCO 44, in turn, is connected both to a second input terminal of comparator 40 and to electrode 26, which functions as the transmission electrode. A frequency-measurement device 45 provides an output indicative of the frequency at which VCO 44 operates; this output may be used for parameter calculation, to drive a display device, etc.

Operation of the circuit is based on the fact that the standing wave condition is characterized by a certain phase relationship between transmitted and reflected waves. This condition is maintained by the phase-locked loop 36. The approximate output frequency of VCO 44 is set for a particular application when the system is manufactured or selected by the user. The precise output frequency, however, is determined by the filtered response of comparator 40. A cylindrical standing wave is established by adjusting the frequency of VCO 44 until a peak output voltage from detection electrode 28 is obtained, or until an inflection point of a phase-frequency plot is reached. Either condition arises as a result of resonance, which is associated with the standing wave condition and therefore indicates its presence. Phase-locked loop 36 is operated to maintain the phase existing at detection electrode 28 when resonance is reached. The circuit is configured to maintain the appropriate phase relationship despite variations in temperature or other conditions that alter the sound velocity, and therefore the resonance wavelength, of the liquid. Such variations produce compensating changes in the frequency output of VCO 44.

Once the resonance point has been obtained, phase shifter 35 is used to alter the output frequency of VCO to bring the resonator to the two frequencies corresponding to the half-power levels that flank each resonance frequency. The half-power level is reached when the phase difference between transmitted and received signals are shifted ±45° with respect to the center of resonance. Accordingly, the phase shifter is operated so as to create these conditions by providing to phase-locked loop 36 successive outputs that are appropriately shifted with respect to the phase corresponding to the center of resonance.

Figure 2:
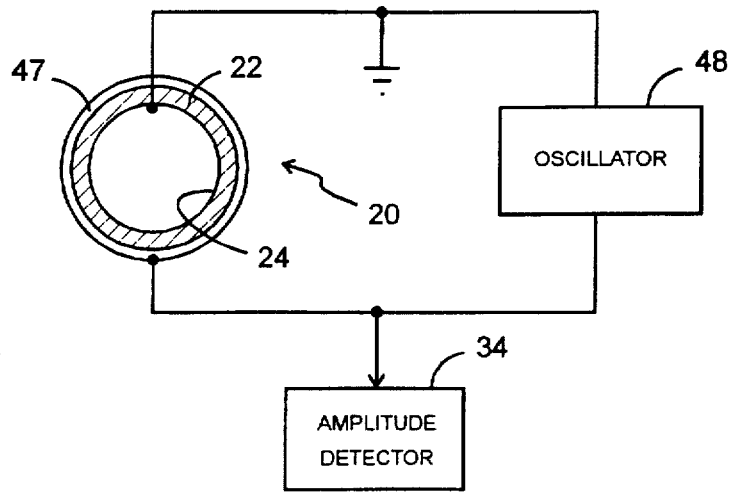
FIG. 2 schematically illustrates a second embodiment of the inventive resonator, which features two electrodes.

It is also possible to utilize a transducer design featuring a single outer electrode 47 as part of a feedback oscillator 48, as illustrated in FIG. 2. The transducer functions as the frequency-determining element of the oscillator. Constraining the oscillator to operate in the frequency region of the desired resonance condition (e.g., by filter circuitry, as discussed below) will result in production of a cylindrical standing wave. Because the transducer forms a part of the oscillator circuit, the standing wave will be maintained notwithstanding drift of the resonance wavelength with temperature. Suitable oscillation circuitry is well-known in the art, as exemplified in Sarvazyan, "Development of Methods of Precise Ultrasonic Measurements in Small Volumes of Liquids," Ultrasonics, July 1982, at 151–54 (the disclosure of which is hereby incorporated by reference).

Refer now to FIGS. 3A–3D, which illustrate various configurations of the above resonator embodiments in accordance with the present invention. Each configuration utilizes at least two resonators connected in parallel. The parallel resonators not only fail to interfere with one another, but also provide mutual compensation that obviates the need for the correction circuits ordinarily required for single-cell designs. Ordinarily, one resonator contains the solution under study and the other contains a reference liquid (typically the pure solvent). So long as the resonant frequencies of the two resonators are well-separated (e.g., by 10 or more times the half-power frequency bandwidth), their parallel connection will not interfere with measurement. The second resonator, even if not filled with a reference liquid, functions as a balancing element in the circuit that compensates for the frequency dependences of the electromechanical parameters of the measuring resonator.

Figure 3B:
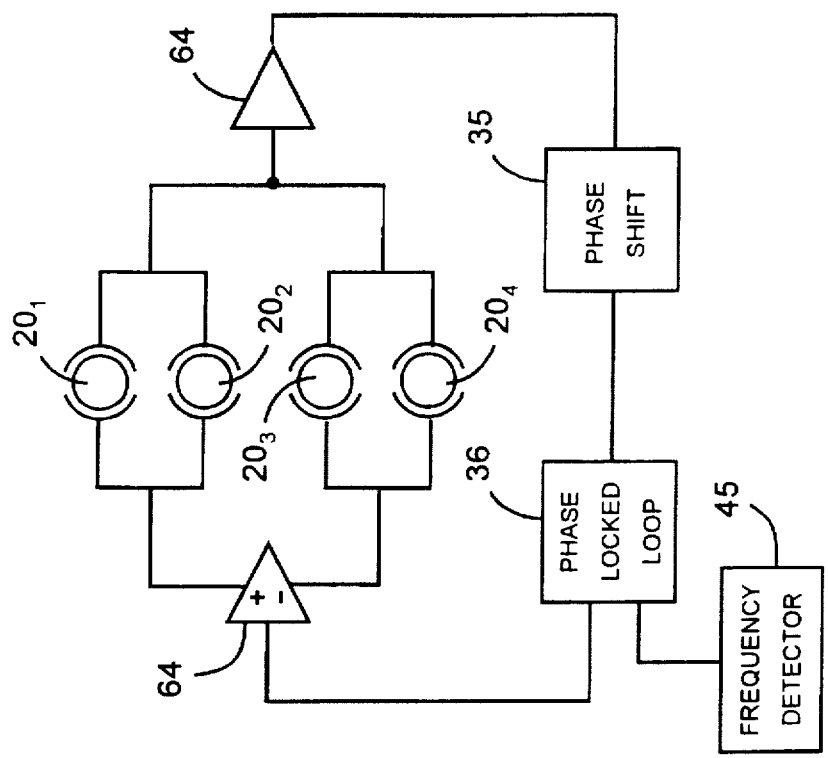
FIGS. 3A–3D schematically illustrate various combination circuits including the resonators depicted in FIGS. 1 and 2.
Figure 3A:
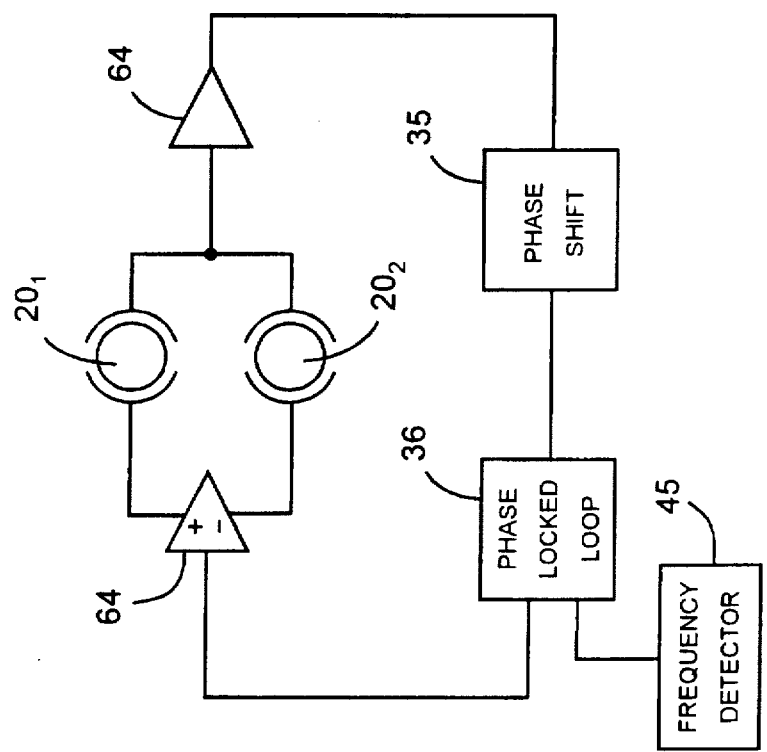

In FIGS. 3A and 3B, the detection electrodes of two to four resonator cells $20_1$, $20_2$, $20_3$, $20_4$ are connected to the phase shifter 35 and the phase-locked loop 36 described earlier (but which should provide integration capability). The resonance condition is ordinarily established for a given application and set during manufacture by selection of phase conditions corresponding to the appropriate frequency of oscillation. Alternatively, the device may be constructed to permit the user to adjust oscillation frequency until a peak output voltage is obtained, or until an inflection point of a phase-frequency plot is reached; phase shifter 35 is set so that phase-locked loop 36 maintains the phase associated with the resonance frequency. Half-power frequency measurements can be made by varying the phase to ±45° with respect to the resonance phase, and noting the output frequencies of VCO 44.

FIG. 3B illustrates the flexibility of this design, which can be extended to two or more pairs of resonator cells $20_1$, $20_2$, $20_3$, $20_4$ so long as sufficient separation between the resonance peaks is assured. If the resonators are to contain acoustically similar liquids, it is possible to manufacture the cells with slightly different geometries to ensure sufficient separation of resonance frequencies.

Figure 3D:
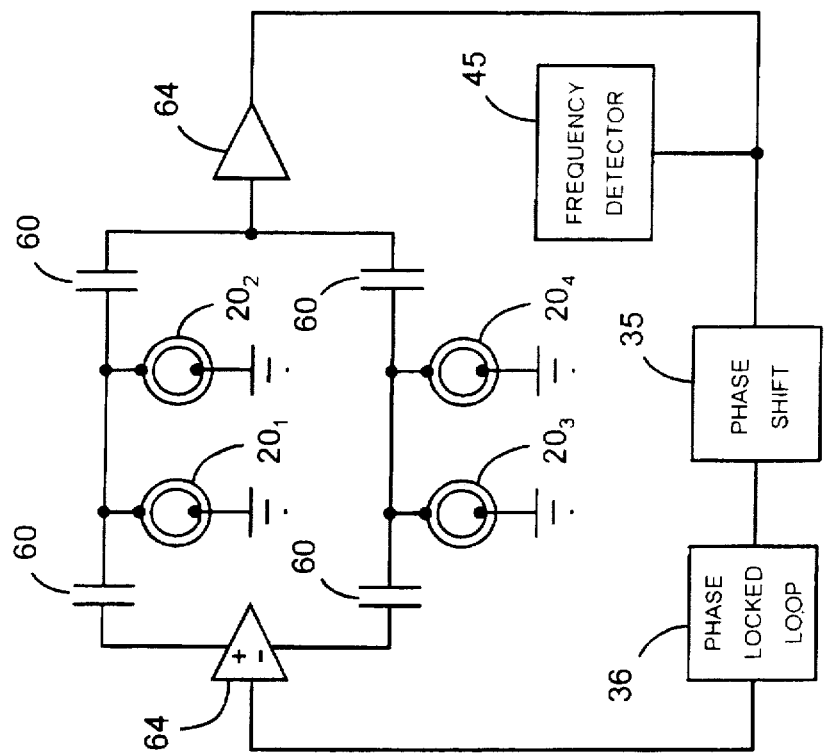
Figure 3C:
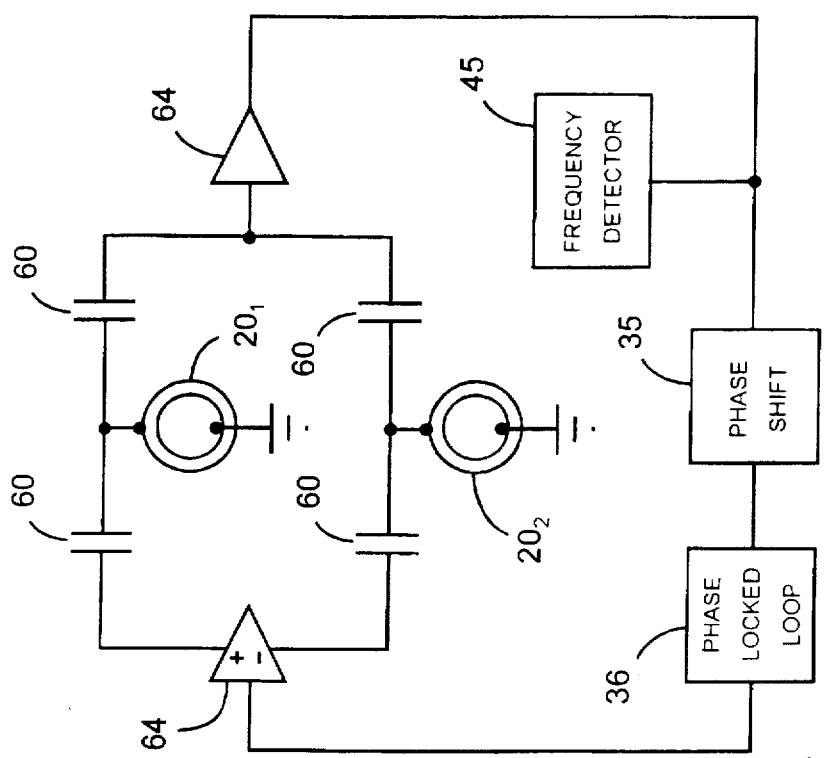

FIGS. 3C and 3D illustrate parallel implementations of the resonator embodiment shown in FIG. 2. The resonator cells $20_1$, $20_2$, $20_3$, $20_4$ each contain a single outer electrode and a grounded inner electrode. The outer electrodes are connected, via a series of capacitors denoted generally by reference numeral 60, to the input terminal of an amplifier 64 and to the inverting and non-inverting output terminals of a second amplifier 66. The output of amplifier 64 is fed back to amplifier 66 by way of a phase-locked loop 36 and a phase shifter 35. With particular reference to FIG. 3C, leaving both resonators $20_1$, $20_2$ empty or filling them with the same fluid results in precise cancellation of the electrical signals from amplifier 66, since their magnitudes will be equivalent and their phases opposite; the result is zero voltage at the input of amplifier 64.

When one of the cells resonates, the resulting voltage at the input to amplifier 64 is very large and due almost entirely to the resonating cell. Once again, phase conditions corresponding to the resonance condition are established and fixed during manufacture or by the user. Phase-locked loop 36 maintains this condition, and the frequency indicated by the measurement device 45 will then be the resonant frequency of the sample contained in the resonating cell. Phase shifter 35, which may be located on either side of phase-locked loop 36, is used to confine circuit operation to the resonance condition.

2. Preferred Device Implementations

Figure 4:
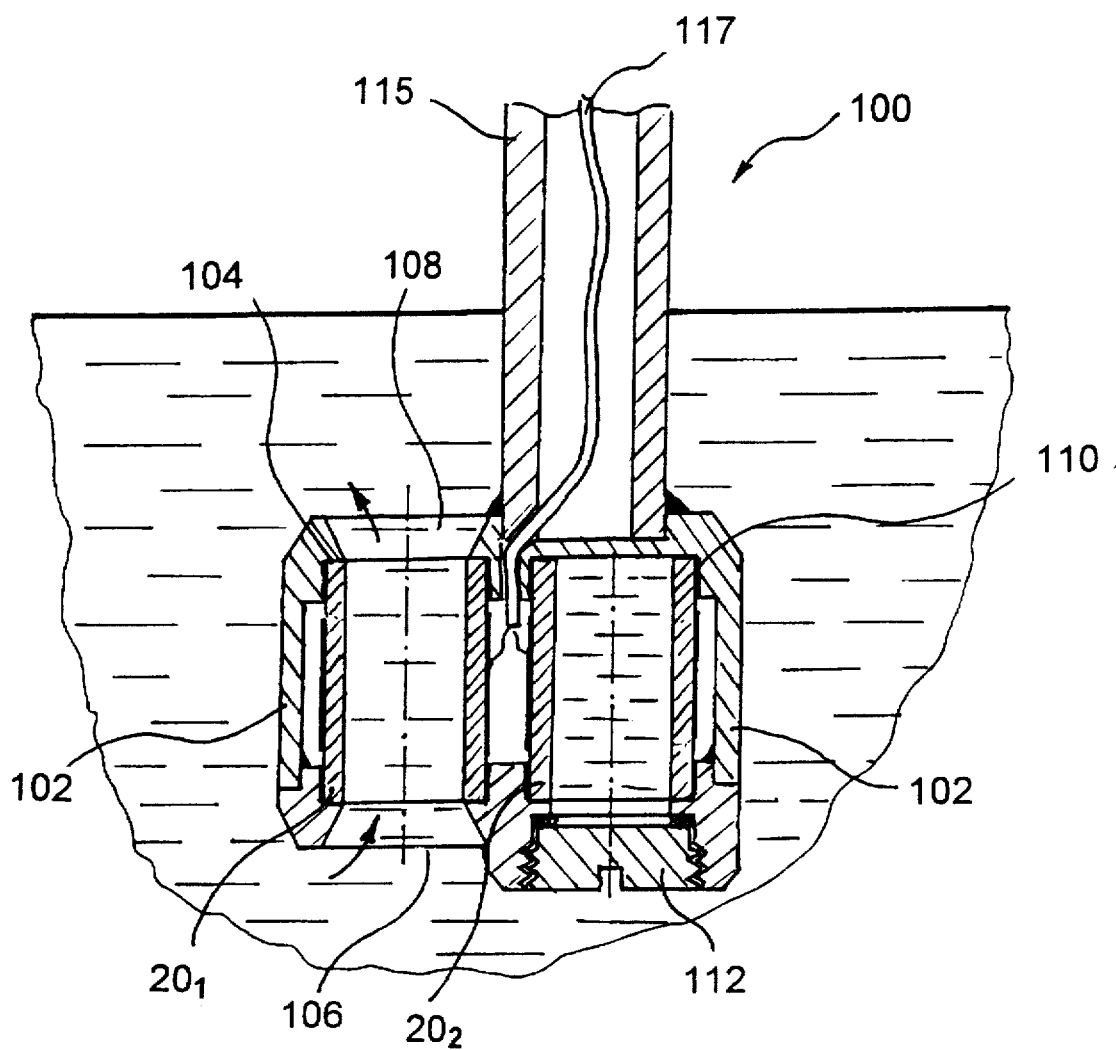
FIG. 4 is a sectional elevation of a "dip-in" probe based on the circuit shown in FIG. 3A or 3C.

A representative dip-in probe embodying dual matched transducers, as shown in FIGS. 3A and 3C, is illustrated in FIG. 4. The probe comprises a housing 102 having therein cylindrical cavities that each accommodate a resonator and open into a window therebetween. A first cavity 104 contains a first resonator $20_1$, and is collared over the resonator ends to create a pair of apertures 106, 108 that, together with resonator $20_1$, define a flow channel. Accordingly, when immersed in a liquid as shown in the figure, the liquid is free to flow through the resonator as indicated by the arrows. A second cavity 110 contains a second resonator $20_2$. Unlike the first resonator, resonator $20_2$ is fluidically sealed within cavity 110 by means of a gasketed upper wall and a threaded, removable cap 112. Cap 112 screws into the lower extremity of cavity 110 and seals by means of a gasket or the like.

Housing 102 is sealably joined to an elongated conduit 115, which carries one or more cables 117 that connect resonators $20_1$, $20_2$ to the electrical circuitry described previously. Cable 117 passes through housing 102 into the window therebetween, where it is electrically connected to the electrodes of both resonators.

In operation, with cap 112 removed, resonator $20_2$ is filled with a reference solution and cap 112 then replaced. The probe 100 is immersed in a sample solution, and the circuitry of FIG. 3A or 3C operated to create cylindrical standing waves in each of the resonators. For attenuation and velocimetric studies, the resonance and the half-power frequencies are measured for one or more resonances. It should be emphasized that while this and ensuing figures depict implementations that feature a single pair of resonators, this is for convenience of illustration only; multiple pairs of resonators can be introduced by straightforward modification of the depicted designs.

Figures 5A, 5B:
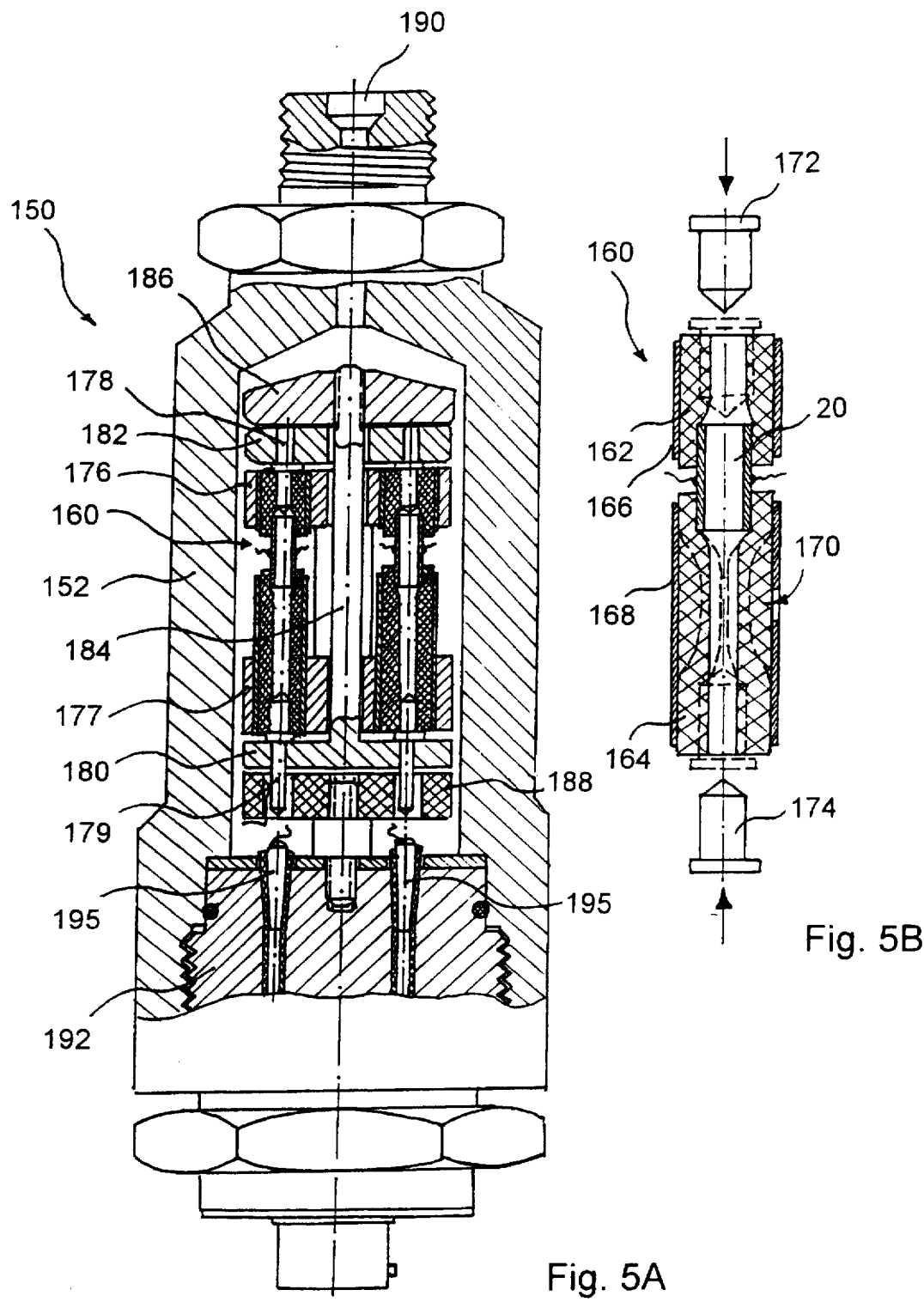
FIG. 5A is a partial cutaway elevation of a high-pressure vessel incorporating at least two resonators embodying the present invention.
FIG. 5B is an enlarged sectional detail of a resonator assembly from the device shown in FIG. 5A.

FIG. 5A illustrates incorporation of the resonators of the present invention into a sealed vessel that accommodates measurement of fluid characteristics at high pressures. The measurement device 150 includes a rigid shell 152 whose interior holds at least one pair of resonator assemblies, whose construction is detailed in FIG. 5B. Each resonator assembly 160 includes a resonator cell 20 whose ends are fitted tightly within a pair of elastomeric sleeves 162, 164. Each sleeve is itself surrounded by a protective metal jacket 166, 168. A slot 170 through part of the perimeter of jacket 168 exposes a portion of sleeve 164 to the surrounding high-pressure atmosphere within shell 152. The space between sleeves 162, 164 exposes a portion of resonator 20 to accommodate electrical connection. The ends of sleeves 162, 164 opposite the resonator 20 are sealed by a pair of tightly fitting plugs 172, 174.

With reference to FIG. 5A, the sealed resonator assemblies are carried within an opposed pair of cups 176, 177, which receive the ends of metal jackets 166, 168. Projecting outwardly from the base of each cup 176, 177 is a mounting pin 178, 179. The cups are borne on a mounting bracket that includes a pair of opposed retaining platforms 180, 182, each of which contains a bore for receiving a pin 178, 179. A shaft 184 projects from platform 180 and fits through a central bore in opposed platform 182, terminating in a series of threads that are engaged by a nut 186. Tightening nut 186 anchors the resonator assemblies, whose ends are contained within cups 176, 177, between the platforms. The pin 179 from each lower cup 177 protrudes through platform 180 sufficiently to engage bores through a table 188.

One end of shell 152 contains an inlet 190 that admits pressurized fluid (ordinarily a liquid) into the interior of the shell. The opposite end of shell 152 receives a threaded plug 192 that bears a series of electrical contacts 195 to establish connection between the resonators and external circuitry. The contacts 195 reside within lined, tapered channels that prevent ejection of the contacts as a result of the high-pressure environment. A central depression in the interior face of plug 192 receives one end of a collared shaft, the other end of which projects into a central bore in table 188. The collar spaces the underside of table 188 from the top surfaces of electrical contacts 195, which are wired or otherwise connected to the resonator electrodes. Plug 192 includes an 0-ring or other gasket to provide a pressure seal when the plug is threaded into shell 152.

The foregoing mechanical arrangement allows the resonator assemblies 160 to be secured within the mounting bracket before the latter is coupled to the plug 192. In operation, plugs 172, 174 are removed from each resonator assembly, facilitating the introduction of a liquid sample therein. The removed plugs are then replaced, the resonators are secured within the mounting bracket, electrical connections between contacts 195 and the resonators are established, and the mounting bracket is coupled to plug 192. After plug 192 is threaded into shell 152, pressure-transmitting fluid is admitted into the interior of shell 152 via inlet 190. As the pressure increases, elastic tube 164, which is exposed to the interior atmosphere through slot 170, bows inwardly and thereby communicates the surrounding pressure to the liquid. Resonance acoustic measurements through the liquid under pressure may then be taken.

Figure 6B:
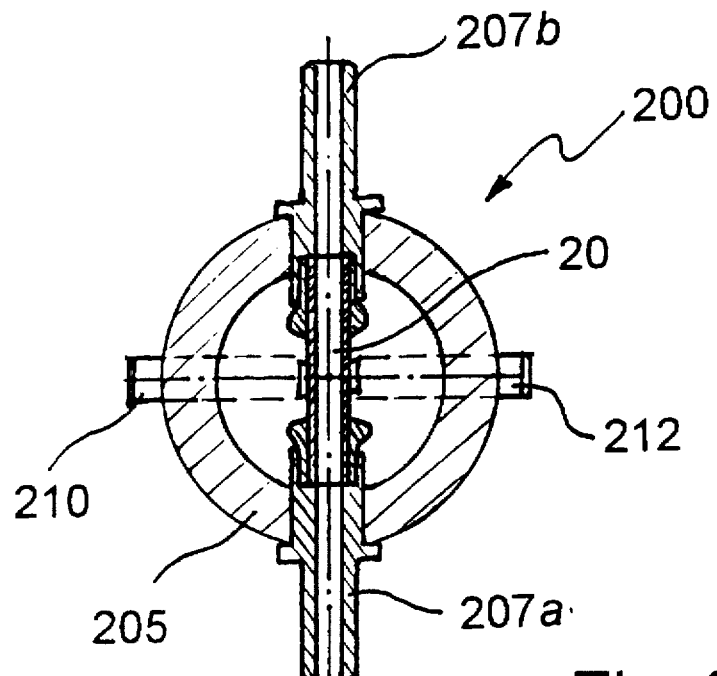
FIG. 6B is a section taken along line B—B of FIG. 6A.
Figure 6A:
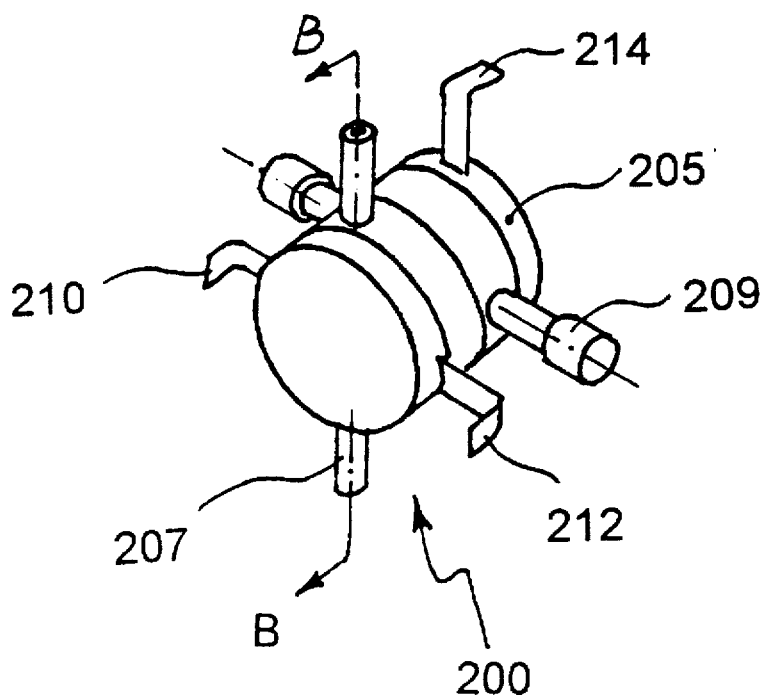
FIG. 6A is an isometric view of a resonator assembly for use in a "fill-in" device.

FIGS. 6A and 6B illustrate a resonator assembly adapted for fill-in applications, where a sample of liquid is suctioned from a reservoir into the resonator channel. The resonator assembly 200 shown in the figures includes a sealed body 205 that carries therein a pair of resonator cells, one of which is connected to a flow tube 207 and the other to a reference-liquid carrier 209. Both of these elements project radially through body 205.

As shown in greater detail in FIG. 6B, flow tube 207 actually consists of a pair of fluid connectors 207a, 207b sealed with respect to the exterior of body 205 and sealably joined to a resonator cell 20 to form a fluid channel therethrough. In the illustrated embodiment, the resonator 20 is the three-electrode embodiment shown in FIG. 2, with inner and outer electrodes connected to a pair of prongs 210, 212 that span body 205.

Reference-liquid carrier 209 is a hollow tube that also includes a resonator cell 20 (not shown) contiguous therewith inside body 205; that resonator, too, is connected to a pair of prongs, one of which is shown at 214, that protrude through body 205 for external connection. Reference-liquid carrier 209, for reasons discussed below, is preferably oriented perpendicularly to flow tube 207, and includes a removable cap at one end. The cap is withdrawn to permit introduction of a sample liquid therein. When replaced, the cap forms a seal that prevents entry into reference-liquid carrier 209 of liquid from the reservoir in which the resonator assembly 200 may be immersed.

Figures 7A, 7B:
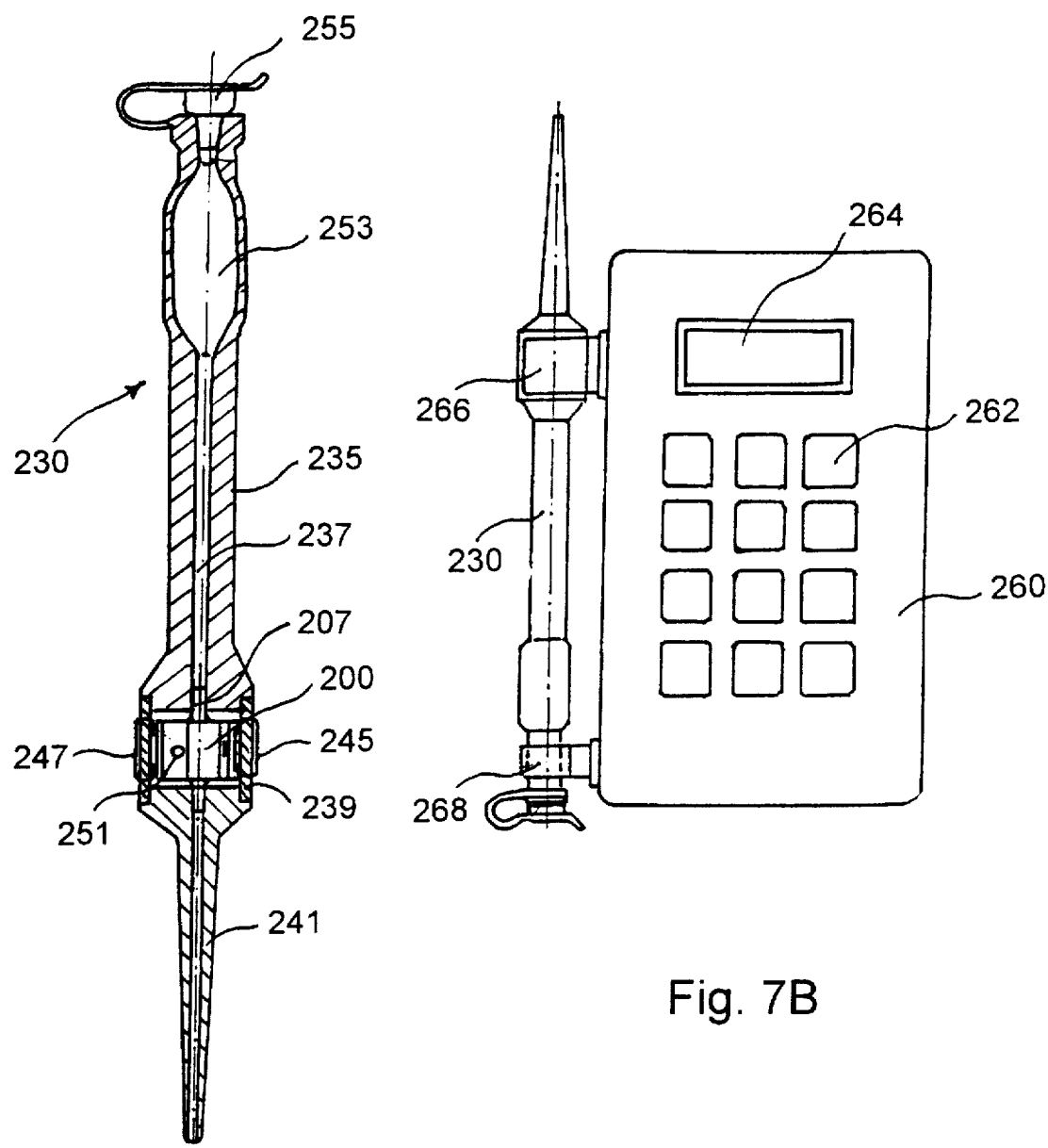
FIG. 7A is a sectional view of a fill-in device that operates by drawing a liquid to be studied into the resonator assembly depicted in FIGS. 6A and 6B.
FIG. 7B is a plan view of a modular construction that includes the device shown in FIG. 7A in combination with a housing that includes display and driver circuitry.

FIG. 7A illustrates a dip-in syringe-type device incorporating the sensor assembly 200. The device 230 includes a first generally tubular segment 235 whose interior bore 237 mates with flow tube 207 of the resonator assembly at a first end, and whose exterior at that end flares outward and forms a ridge to accept the upper edge of a cylindrical wall 239. The lower edge of wall 239 is sealably joined to a similar ridge in a second, tapered tubular segment 241, the bore of which mates with the other end of flow tube 207. The fluid-tight chamber thus formed within wall 239 contains the resonator assembly 200.

For this application, the resonator design of FIG. 3A or 3B is preferred. In this case the prongs connected to the common resonator electrodes are connected together, and these prong sets are soldered to a pair of opposed contact plates 245, 247 that clip through slots in wall 239. At least the removably capped end of reference-liquid carrier 239 is long enough to protrude through an aperture 251 in wall 239.

The other end of tube segment 235 widens in its interior to form a compressible bladder 253. The top of tube segment 235 is closed by a removal cap 255.

By means of its exposed electrical contacts, the illustrated configuration may be joined directly to a housing 260 that contains the circuitry discussed above in connection with the resonator cells, as well as control and display elements tailored to a particular application. For example, using programmable microcomputer circuitry, it is possible to implement selectable control protocols that perform user-specified measurements and calculate desired acoustic parameters. Thus, using keyboard 262, the user may first obtain readings from one or more samples of known concentration and electronically store these, along with the associated concentrations, as calibration points; then, switching modes from calibration to measurement, the user may obtain a reading from an unknown sample and, based on the stored calibration points, compute the concentration of the sample for display. In other measurement modes of operation, the user may select attenuation (in which case the display 264, in conjunction with appropriate circuitry, serves the function of measurement device 34) or acoustic velocity (in which case peak and half-power frequency measurements are taken from the sample and the reference solutions, and a velocity calculated as discussed above) or resonance frequency (in which case display 264, in conjunction with appropriate circuitry, serves the function of measurement device 45). The programming and circuitry to implement the foregoing functions are straightforwardly realized without undue experimentation by those skilled in the art.

Electrical connection between contacts 245, 247 and the circuitry within housing 260 is made via complementary contacts on the interior surface of a clamp 266, facilitating convenient docking of the device 230. A second clamp 268 grips upper portion of device 230. In operation, the user first introduces a reference liquid into carrier 209. The user then compresses bladder 253 and immerses the inlet to tube 241 into a reservoir of the liquid under study. Releasing the bladder draws liquid into flow tube 207, and the vacuum thereby created prevents its release. The filled device may then coupled with housing 260 as described above.

A variety of modifications to this basic configuration are possible. A more rugged, precise syringe design can include a spring-loaded plunger that retracts to withdraw precisely the amount of sample liquid necessary to fill the resonator cell. Composite devices including multiple syringe elements, simultaneously operated by plungers joined to a common yoke, are useful in performing analyses of biological samples contained in microtiter plates. The resonator embodiments illustrated in FIGS. 3B and 3D are especially useful with such composite devices.

Figure 8A:
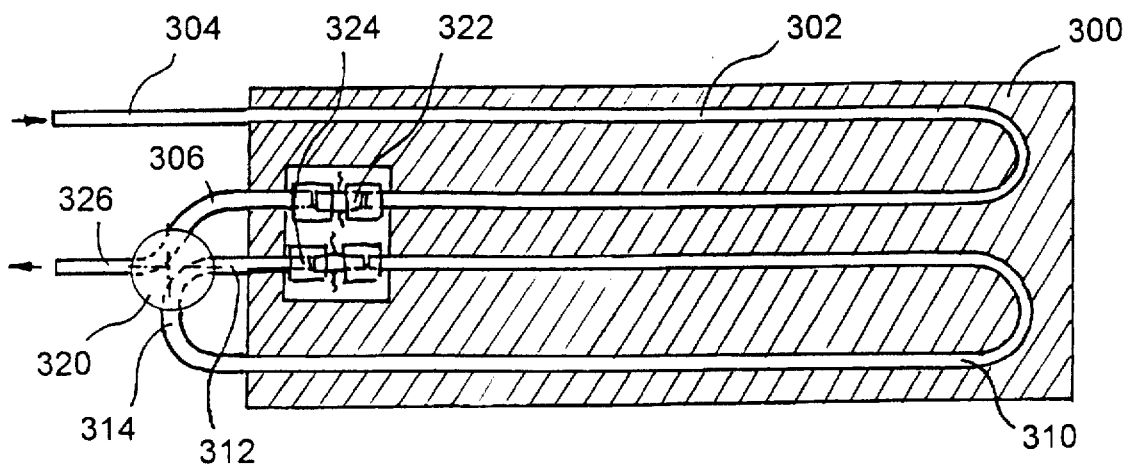
FIG. 8A is a plan view of the flow-through embodiment of the present invention.
Figure 8B:
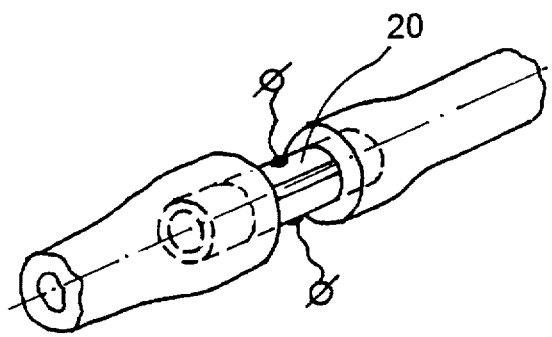
FIG. 8B is an enlarged isometric view of the sensor and its coupling in accordance with the embodiment depicted in FIG. 8A.
Figure 8C:
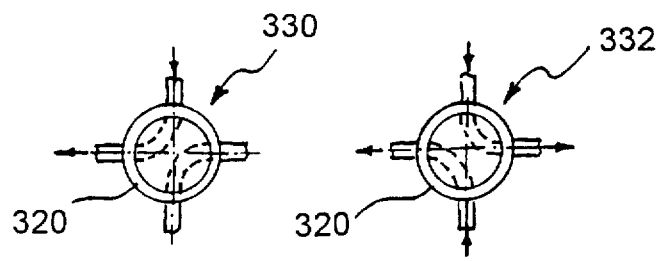
FIG. 8C illustrates the configuration and operation of the four-port valve used in the embodiment depicted in FIG. 8A.

Another useful configuration embodying the present invention is illustrated in FIGS. 8A–8C. This flow-through embodiment permits continuous monitoring of a liquid stream whose composition changes over time. Such capability is of particular value, for example, in analyzing effluent from separation columns, liquid chromatography columns, and flow streams from chemical and pharmaceutical manufacturing processes, where even small compositional changes can prove critical. The apparatus is mounted on a support block or structure 300, and includes a first flow tube 302 having ends 304, 306; a second flow tube 310 having ends 312, 314; a four-port valve 320 for selectably connecting the tube ends; and a pair of sensor elements 322, 324, each associated with one of the flow tubes; and an outlet tube 326.

FIG. 8B shows a sensor element in greater detail. The element includes a resonator cell 20, the electrodes of which are wired to external circuitry as described previously. The resonator 20 intervenes along and is contiguous with its associated flow tube to maintain a continuous fluidic pathway therethrough, and is sealably joined at each end to spaced-apart sections of the tube.

The four-port valve, as shown in FIG. 8C, contains interior elbow joints and controls the connections among tube ends 306, 312 and 314, and outlet tube 326. In a first position 330 (also illustrated in FIG. 8A), end 306 of flow tube 302 is connected to outlet tube 326, while tube 3 10 forms a closed loop. In a second position 332, flow tubes 302 and 310 join one another to form a continuous fluid path from inlet 304 to outlet tube 326.

In operation, valve 320 is initially set to the second position 332, and a reference liquid introduced into inlet 304 until it is observed exiting outlet tube 326. At this point, liquid occupies the entire flow path. Valve 320 is then shifted to position 332, trapping the reference liquid within the closed loop of tube 310. Sample liquid entering inlet 304 eventually displaces the reference liquid. The acoustic characteristics of the sample liquid can be continuously monitored against the trapped reference liquid.

Figure 9:
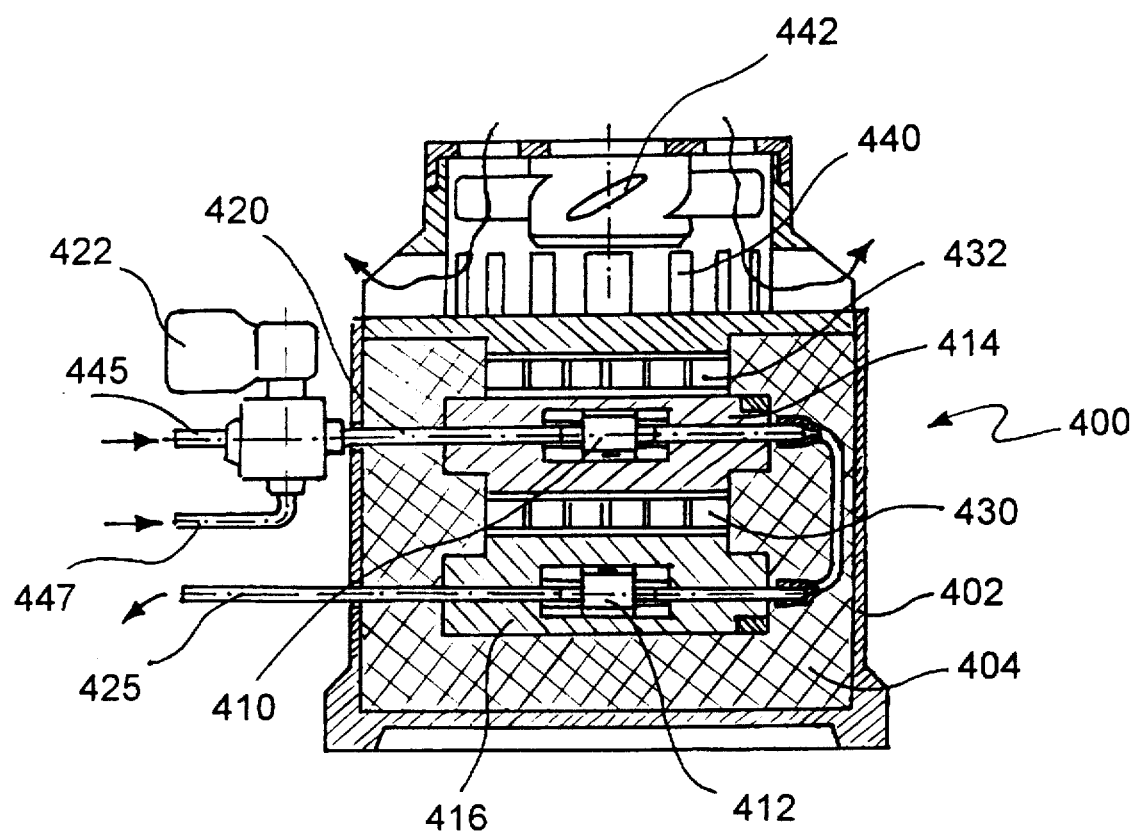
FIG. 9 is a sectional elevation of an embodiment that permits simultaneous measurement of the acoustic parameters of a liquid at different temperatures.

FIG. 9 illustrates an implementation of the invention that facilitates acoustic analysis of a liquid at multiple temperatures. This capability permits, for example, simultaneous analysis of multiple physical characteristics that each exert an acoustic effect. For example, the fat content of milk cannot be assessed using measurements of the speed of sound and attenuation at a single temperature, since both nonfat solids and fat independently contribute to changes in these acoustic parameters. However, the temperature dependence of these parameters are different for nonfat solids and fat (the former being more strongly dependent on temperature), so measurements of both the overall speed of sound at different temperatures specify the individual levels of each type of material.

As shown in the figure, the device 400 includes a sturdy, thermally conductive (e.g., metal) outer housing 402, partially filled with an insulating material 404 (such as rubber or fiberglass) to form a cavity therein. Contained within the cavity are first and second resonator cells 410, 412, each housed within a thermally conductive casing 414, 416. The individual resonator cells 410, 412 each include a resonator cell 20 packaged so as to be in thermal communication with the associated casing 414, 416. The resonator cells 20 intervene along and are contiguous with a flow tube 420, which draws liquid from a three-way stopcock valve 422 and ejects it from an outlet 425. Sandwiched between casings 414 and 416 is a first Peltier element 430. A second Peltier element 432 is disposed above casing 414, sandwiched between this casing and an inner wall of housing 402. The Peltier elements are thermoelectric devices comprising a junction of two dissimilar metals; a current flowing through the junction causes either absorption or liberation of heat, depending on the direction of the current, in approximate proportion to its magnitude. In the present invention, the devices are used in combination to maintain a controllable, fixed temperature difference between casing 414 and 416. Specifically, Peltier element 430 is controlled to maintain the fixed temperature differential (for example, 5° C., in the case of milk analysis) between casing 414 and 416, with 416 maintained at the hotter temperature; and Peltier element 432 is operated as a heat pump to maintain casing 414 at a selected temperature, conducting excess heat to housing 402 and a series of cooling fins 440 thereon. The temperature monitoring and feedback circuitry necessary to accomplish these actions is well-known by those skilled in the art.

The efficiency of convective heat removal from the cooling fins 440 may be further enhanced by locating a fan 442 thereabove and directing its airflow against the fins.

Valve 422 accepts incoming liquid from either of two inlet tubes 445, 447. In operation, one of these tubes carries the sample liquid, and the other a flush liquid. Valve 442 is initially set to admit the sample liquid, which is provided until both resonator cells are filled. Before measurements are made, the liquid is allowed to reside in the cells until Peltier elements 430, 432 re-establish the desired temperature. The resonators are then controlled, as discussed previously, to measure one or more acoustic parameters of the sample liquid. After the measurements have been taken, valve 422 is switched to admit flush liquid, which cleans the system.

Figure 10:
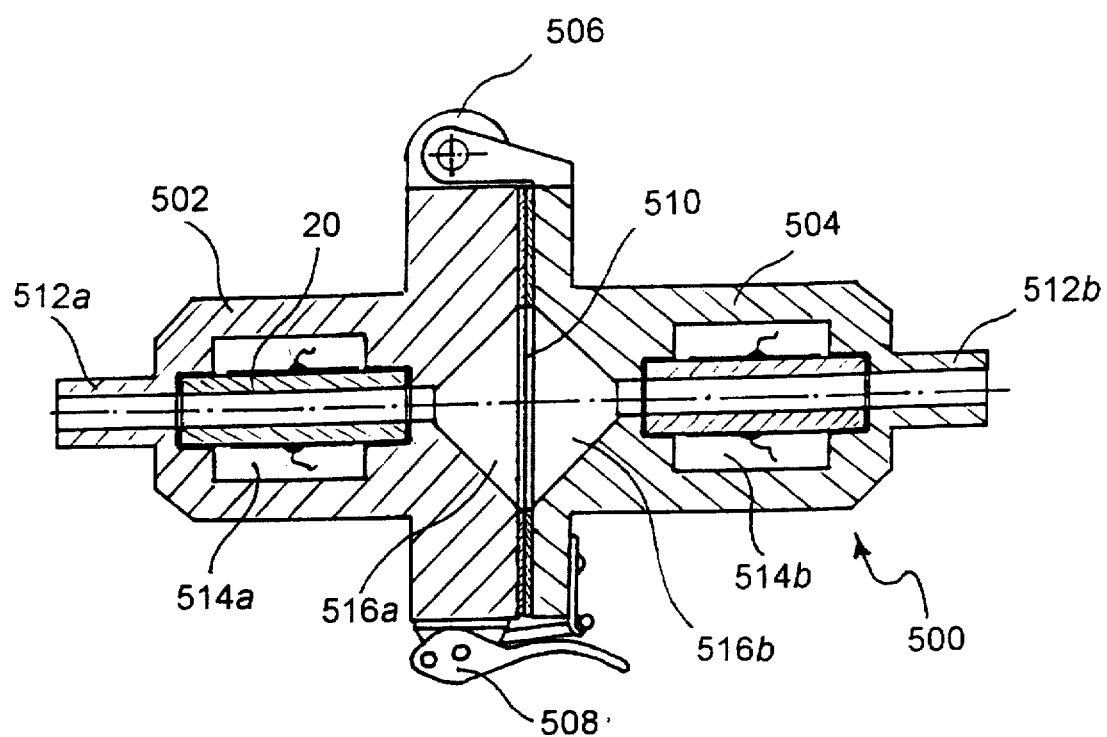
FIG. 10 is a sectional elevation of an embodiment that permits simultaneous measurement of the acoustic parameters of particles in suspension.

In some cases it is useful to measure the concentration not of dissolved substances, but of particles in suspension (e.g., biological cells in a culturing medium). In such cases, the total concentration of particles is ordinarily small compared with the concentration of molecules or ions in a typical solution, and their contribution to the speed of sound is therefore one or two orders of magnitude lower than that of dissolved substances. Accordingly, to use acoustic techniques to measure the concentration of particles suspended in a liquid that itself contains dissolved substances, it is necessary to subtract the much larger acoustic contribution of the dissolved substances themselves. The embodiment illustrated in FIG. 10 is a fixture that facilitates this procedure by allowing simultaneous acoustic analysis of a particle suspension and the pure, particle-free carrier liquid.

The fixture 500 includes oppositely oriented resonator enclosures 502, 504 affixed by means of a hinge 506 and a releasable fastening clip 508. Hinge 506 and clip 508 are mounted so as to accommodate but firmly retain, upon closure, a membrane filter 510 between enclosures 502, 504. Each enclosure includes an inlet port 512a, 512b and a cavity 514a, 514b. Mounted within each cavity 514a, 514b is a resonator cell 20. Electrical connection to the electrodes of the resonator cells 20 can be facilitated, for example, by wiring them to external plate contacts or plugs on the outer surface of enclosures 502, 504.

Each cavity 514a, 514b widens past the side opposite the inlet port to define a conical reservoir 516a, 516b. The resonators 20 are mounted within the cavities so as to define a continuous fluidic pathway, interrupted only by membrane filter 510, between inlet ports. In operation, the particle-containing liquid is introduced into one of the inlets 512a, 512b. Particles cannot traverse membrane filter 510, and are thereby prevented from entering the other resonator enclosure. The carrier liquid, however, passes freely through filter 510, eventually filling resonator associated with the other inlet, where it exits. At this point the flow is stopped so that particles, which build up within the reservoir associated with the first inlet, do not back up into the associated resonator and distort acoustic measurements. Those measurements are taken in the manner heretofore described.

As an alternative to the membrane, one or both of the resonators can be configured as shown in FIG. 2 of copending application Ser. No. 08/241,296 filed on May 11, 1994, entitled METHOD AND APPARATUS FOR MANIPULATING, ANALYZING AND SELECTIVELY ISOLATING SUSPENDED PARTICLES USING CYLINDRICAL ULTRASONIC STANDING WAVES (filed contemporaneously herewith and hereby incorporated by reference). In this case a first set of resonator electrodes is used to retain particles within a cylindrical standing wave, preventing their travel to the other resonator, while a second set of electrodes produce a cylindrical standing wave used to measure the acoustic parameters under investigation.

It will therefore be seen that we have developed highly versatile methods and apparatus for the evaluation of acoustic parameters associated with liquids under various conditions. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. Apparatus for measuring acoustic parameters of a fluid, the apparatus comprising:

at least one pair of tubular cells;

means for generating acoustic oscillations within the cells so as to produce a cylindrical mode of oscillation in at least one cell;

means for detecting cylindrical-mode oscillations in the cells; and means for providing, based on the detected cylindrical-mode oscillations, an acoustic parameter measurement;

wherein the mode of oscillation is a cylindrical standing wave;

said apparatus further comprising:
      a sealable chamber, housing a first tubular cell, for receiving a reference liquid;
      a second chamber, housing a second tubular cell, having an inlet and an outlet defining a fluid pathway through the cell;
      measurement means for measuring at least resonance frequency; and
      control means, coupled to the feedback means and to the measurement means, for controlling the signal to maintain a cylindrical ultrasonic standing wave through each cell and performing at least one measurement thereon.

2. The apparatus of claim 1 further comprising feedback means, coupled to the generating means and to the detecting means, for controlling the oscillations to maintain the cylindrical ultrasonic standing wave in at least one cell.

3. The apparatus of claim 1, wherein the cells comprise cylindrical, nonpiezoelectric tubes in contact with a piezoelectric material.

4. The apparatus of claim 1, wherein the cells comprise cylindrical, radially polarized piezoceramic tubes.

5. The apparatus of claim 4 wherein the tubular cells have inner and outer surfaces and include a pair of circumferential electrodes spaced apart from one another and disposed about the outer surface, and a grounded inner electrode disposed about the inner surface.

6. The apparatus of claim 4, wherein the tubular cells have inner and outer surfaces and include an outer electrode disposed about the outer surface, and a grounded inner electrode disposed about the inner surface.

7. The apparatus of claim 2, wherein the feedback means is a phase-locked loop.

8. The apparatus of claim 2, wherein the feedback means is a feedback oscillator in which at least one of the tubular cells is a frequency-determining element.

9. The apparatus of claim 8, wherein tile feedback oscillator includes a pair of amplifiers, one of which has inverting and non-inverting outputs, each of which is connected to one of the tubular cells.

10. The apparatus of claim 1 wherein the second chamber is immersible in a reservoir of sample liquid.

11. The apparatus of claim 1 further comprising:

means for subjecting liquid contained in the tubular cells to elevated pressure;

measurement means for measuring at least resonance frequency; and control means, coupled to the feedback means and the measurement means, for controlling the signal to maintain a cylindrical ultrasonic standing wave through each cell and performing at least one measurement thereon.

12. The apparatus of claim 1 further comprising syringe means for housing the second chamber, the syringe means comprising:

conduit means establishing a fluidic pathway between the second chamber and an elongated inlet; and means for causing liquid to be drawn into the inlet and conducted to the second chamber.

13. The apparatus of claim 12, further comprising an external housing for containing the generating means, the detecting means, the measurement providing means, the control means and the feedback means, all said means being releasably and electrically connected to the tubular cells.

14. Apparatus for measuring acoustic parameters of a fluid, the apparatus comprising:

at least one pair of tubular cells;

means for generating acoustic oscillations within the cells so as to produce a cylindrical mode of oscillation in at least one cell:

means for detecting cylindrical-mode oscillations in the cells; and means for providing, based on the detected cylindrical-mode oscillations, an acoustic parameter measurement;

wherein the mode of oscillation is a cylindrical standing wave:

said apparatus further comprising:

a first chamber, housing a first tubular cell, for receiving a reference liquid;

a second chamber, housing a second tubular cell, having an inlet and an outlet defining a fluid pathway through the cell;

a conduit for carrying a continuous flow of liquid through the second chamber;

measurement means for measuring at least resonance frequency; and control means, coupled to the feedback means and the measurement means, for controlling the signal to maintain a cylindrical ultrasonic standing wave through each cell and performing at least one measurement thereon.

15. The apparatus of claim 14, wherein the conduit includes a valve having a first setting that directs the flow of liquid through the first and second chambers and a second setting that directs the flow of liquid through the first chamber only and forms a closed fluid loop through the second chamber.

16. Apparatus for measuring acoustic parameters of a fluid, the apparatus comprising:

at least one pair of tubular cells;

means for generating acoustic oscillations within the cells so as to produce a cylindrical mode of oscillation in at least one cell;

means for detecting cylindrical-mode oscillations in the cells: and means for providing, based on the detected cylindrical-mode oscillations, an acoustic parameter measurement;

wherein the mode of oscillation is a cylindrical standing wave;

said apparatus further comprising:

a first chamber, housing a first tubular cell, for receiving a reference liquid;

a second chamber, housing a second tubular cell, having an inlet and an outlet defining a fluid pathway through the cell;

a conduit for carrying a continuous flow of liquid through the first and second chambers;

means for establishing a predetermined temperature difference between the first and second chambers;

measurement means for measuring at least resonance frequency; and control means, coupled to the feedback means and the measurement means, for controlling the signal to maintain a cylindrical ultrasonic standing wave through each cell and performing at least one measurement thereon.

17. The apparatus of claim 16, wherein the means for establishing a predetermined temperature difference comprises a pair of Peltier elements.

18. Apparatus for measuring acoustic parameters of a fluid, the apparatus comprising:

at least one pair of tubular cells;

means for generating acoustic oscillations within the cells so as to produce a cylindrical mode of oscillation in at least one cell;

means for detecting cylindrical-mode oscillations in the cells; and means for providing, based on the detected cylindrical-mode oscillations, an acoustic parameter measurement;

wherein the mode of oscillation is a cylindrical standing wave;

said apparatus further comprising:

a first hollow resonator enclosure having a face and housing a first tubular cell for receiving a reference liquid;

a second hollow resonator enclosure housing a second tubular cell and having a face oppositely oriented with respect to the face of the first hollow resonator enclosure so as to form a fluidic pathway through both of said enclosures;

a membrane filter extending across the fluidic pathway between the enclosures;

measurement means for measuring at least resonance frequency; and control means, coupled to the feedback means and the measurement means, for controlling the signal to maintain a cylindrical ultrasonic standing wave through each cell and performing at least one measurement thereon.

* * * * *

UNITED STATES PATENT AND TRADEMARK OFFICE
CERTIFICATE OF CORRECTION

PATENT NO. : 5,533,402
DATED : July 9, 1996
INVENTOR(S) : Sarvazyan, et al

It is certified that error appears in the above-indentified patent and that said Letters Patent is hereby corrected as shown below:

Column 13, claim 9, line 59, delete "tile" and insert --the--.

Signed and Sealed this

Tenth Day of December, 1996

Attest:

BRUCE LEHMAN

Attesting Officer

Commissioner of Patents and Trademarks